United States Patent [19]

Larm

[11] Patent Number: 5,711,938
[45] Date of Patent: Jan. 27, 1998

[54] ORAL HYGIENE COMPOSITION

[75] Inventor: Olle Larm, Bromma, Sweden

[73] Assignee: Medicarb AB, Bromma, Sweden

[21] Appl. No.: 737,010

[22] PCT Filed: Apr. 28, 1995

[86] PCT No.: PCT/SE95/00476

§ 371 Date: Oct. 31, 1996

§ 102(e) Date: Oct. 31, 1996

[87] PCT Pub. No.: WO95/30403

PCT Pub. Date: Nov. 16, 1995

[30] Foreign Application Priority Data

May 4, 1994 [SE] Sweden ................ 9401540

[51] Int. Cl.⁶ .............. A61K 7/16; A61K 9/14; A61K 9/90; A61K 31/725
[52] U.S. Cl. .............................. 424/49; 424/435
[58] Field of Search ................ 424/49, 435

[56] References Cited

U.S. PATENT DOCUMENTS

| | | | |
|---|---|---|---|
| 4,512,968 | 4/1985 | Komiyama et al. | 424/49 |
| 4,767,463 | 8/1988 | Brode et al. | 106/162 |
| 4,879,281 | 11/1989 | Shibasaki et al. | 514/55 |
| 4,925,677 | 5/1990 | Feijen | 424/484 |
| 4,933,182 | 6/1990 | Higashi et al. | 424/435 |
| 5,036,056 | 7/1991 | Kludas | 514/54 |
| 5,041,292 | 8/1991 | Feijen | 424/484 |
| 5,049,403 | 9/1991 | Larm et al. | 427/2 |
| 5,055,298 | 10/1991 | Kludas | 424/401 |
| 5,182,103 | 1/1993 | Nakane et al. | 424/49 |
| 5,192,362 | 3/1993 | Harvey et al. | 106/35 |
| 5,213,898 | 5/1993 | Larm et al. | 428/422 |
| 5,290,559 | 3/1994 | Groves | 424/435 |
| 5,554,388 | 9/1996 | Illum | 424/501 |
| 5,645,844 | 7/1997 | Henderson et al. | 424/405 |

FOREIGN PATENT DOCUMENTS

| | | |
|---|---|---|
| 0324720 | 7/1989 | European Pat. Off. |
| 2132889 | 7/1984 | United Kingdom. |
| 2215730 | 9/1989 | United Kingdom. |
| 8404453 | 11/1984 | WIPO. |
| 9312801 | 7/1993 | WIPO. |
| 9416714 | 8/1994 | WIPO. |

OTHER PUBLICATIONS

Solovyeva et al Chem. Abstr. 121(3) #26652 18 Jul., 1994.
Derwent Abstract of Endo JP 59112922 (Jun. 29, 1984).

*Primary Examiner*—Shep K. Rose
*Attorney, Agent, or Firm*—Burns, Doane, Swecker & Mathis, L.L.P.

[57] ABSTRACT

Oral hygiene composition containing in combination chitosan and a sulphated, negatively charged polysaccharide in a biologically active amount; a process of improving oral hygiene in a mammal including man; and use of chitosan in combination with a sulphated, negatively charged polysaccharide for the manufacture of dentally active oral hygiene compositions.

16 Claims, No Drawings

ORAL HYGIENE COMPOSITION

The present invention relates to oral hygiene compositions containing in combination certain polysaccharide components, a process to improve oral hygiene in mammals including man and the use of combinations of polysaccharides for the manufacture of dentally active oral hygiene compositions.

Even if the present invention relates in general to oral hygiene it will primarily be illustrated in connection with periodontitis, i.e. so called teeth loosening, and measures aiming at reducing active plaque, i.e. bacterial deposits on the surface of the tooth.

Periodontitis is a collagen disease resulting in decomposition of the supporting tissue of the tooth, periodontal ligaments and bone tissue. This results in weakening of the attachment apparatus, finally resulting in loosening of the tooth. The tooth loosening procedure is inflammatoric and the cause is found in the bacterial plaques accumulated on the surface of the tooth and against which the immune defense of the body is not capable of adequate defense. P The symptoms in periodontitis is generally in an early stage an inflammatoric change of the gingiva, i.e. the gums, which swells, reddens and becomes lightly bleeding on probing. In the transit from gingivitis to periodontitis, the latter constituting the destructive part of the cause of the disease, the collagenous threads surrounding the attachment, the periodontium, are destroyed, and simultaneously plaques spread down into the periodontal pocket developed during the course of the disease. This results in deepening and inflammation of the pocket, and as the pathological periodontal pocket deepens the tooth loses more and more of its attachment thereby obtaining increased mobility.

The traditional treatment of the disease conditions mainly aim towards active plaques, i.e. bacterial deposits on the surface of the tooth. The self-care of the patient in the form of thorough oral hygiene is of decisive importance in this connection. Usually the mechanical oral hygiene, tooth brushing, and interstitial hygiene using thread or stick, is the most common and effective procedure. However, there are different chemical possibilities of affecting or preventing bacerial growth or bacterial adherence to the tooth.

Professional tooth cleaning using a tooth hygienist and/ or a dentist who removes plaque present and cleans the deep periodontal pockets inaccessible through common tooth cleaning reduces or eliminates the inflammation. If such cleaning of the tooth does not give the desired effect when carried out through the opening of the periodontal pocket a surgical treatment must be carried out. The gums are then folded aside so as to give full access to the pocket thereby enabling thorough cleaning.

By means of different membranes the tissues can be kept apart during the course of healing and the tissue which is desired in healing will have precedence. This techniques are named "Guided Tissue Regeneration", abbreviated GTR. GTR-treatment is presently the only way of providing periodontal healing with renewed growth of periodontal supporting tissue. Since the healing process is controlled by a barrier giving priority to the slow periodontal ligament tissue, it is also conceivable to affect the process by means of substances that can affect the regenerative rate thereof.

Oral compositions for the treatment of inter alia caries, periodontoclasia and foul breath are known. For example, GB,A, 2132889 discloses such oral compositions containing chitosan. Furthermore, oral compositions to inhibit or prevent periodontoclasia and caries containing certain sulphated polysaccharides are previously known from WO,A1, 8404453.

It is also previously known to combat plaque using certain negatively charged polysaccharides, such as from EP,A1, 0 324 720 and GB,A, 2215730.

Pharmaceutical compositions, inter alia in the form of a gel, for example for non-topical wound treatment containing one, two or several glycose aminoglykans, such as heparin, condroitin sulphate and chitosan, are previously known from WO,A1, 9312801. Furthermore, hypoglycaemic compositions for oral administration containing oligo- or polysaccharides of natural origin and derivatives thereof, such as chitosan, condroitin sulphates and heparin, are previously known from STN International, File WPIDS, STN accesion No. 84-198108, JP,A, 59112922. Finally, from Chemical Abstracts, Vol. 121 (No. 3, 18 Jul. 1994) abstract No. 26652, Vopr. Med. Khim., 1994, 40 (2), page 37–39 it is known that the combination of chitson sulphates and heparin affect the activity of lipoprotein lipase.

The present invention has for its purpose to provide new techniques for improved oral hygiene. Another object of the invention is to provide new oral hygiene compositions which substantially improve the conditions to alleviate the inflammatoric process in periodontitis and also to provide recreation of the attachment of the tooth.

Yet another purpose of the invention is to provide oral hygiene compositions which reduce the formation of active plaques on the surface of the tooth.

A further object of the invention is to provide a process to improve oral hygiene in mammals including man.

Yet another object of the invention is to provide use of certain polysaccharides in combination for the manufacture of dentally active oral hygiene compositions.

For these and other objects which will be clear from the following disclosure there is provided through the present invention an oral hygiene composition which in combination comprises chitosan and a sulphated, negatively charged polysaccharide in a biologically active amount.

In the composition according to the invention it is preferred that the weight ratio chitosan:sulphated polysaccharide lies within the range about 6:4 to 95.5:0.5.

Among useful polysaccharides in oral hygiene compositions according to the present invention there may be mentioned heparin, sucralfat, condroitin-6- or -4-sulphates, dermatan sulphate, keratan sulphate and pentosan sulphates.

It is particularly preferred in the oral hygiene composition according to the invention to use chitosan in combination with heparin, the weight ratio between these two components preferably lying within the range about 10:1 to 99.5:0.5.

The oral hygiene composition according to the present invention suitably contains chitosan and sulphated polysaccharide in combination with a dentally acceptable carrier. The oral hygiene composition can be presented in the form of a tooth cream, a tooth paste or in the form of a tooth powder. It may also be presented in the form of a mouth wash or in the form of a mouth spray. Finally, the oral hygiene composition according to the invention can be presented in the form of degradable films, gels, pearls or powders.

The composition according to the present invention is preferably in accordance with one aspect of the invention presented in the form of a tooth cream, a tooth paste or a tooth powder. As an alternative the composition can also be presented in the form of a chewing gum, a tablet, a lozenge or the like. Compositions of these types have, in addition to the special combination of chitosan and a sulphated, negatively charged polysaccharide, a composition corresponding to the conventional techniques in the art. The special combination of the chitosan and sulphated polysaccharide in accordance with the present invention is present in the composition in a suitable minor amount, preferably from about 1 to about 25 percent by weight and particularly from about 5 to about 15 percent by weight based on the composition as a whole.

When the composition is presented in the form of a tooth treatment agent, such as tooth paste, it may also include a grinding agent in accordance with conventional techniques. Such grinding agents can be taken from the traditional tooth agent techniques and be constituted by for example silica, alumina, hydroxyapatite, plastic particles or mixtures thereof. The grinding agent is present in the composition in a minor amount, preferably within the range 5 to 25 percent by weight.

The composition according to the present invention may optionally contain fluoro compounds for providing further anticaries effect. Such fluoro-containing compounds are suitable of an ionic type and can be constituted by a fluoride salt, such as an alkali metal fluoride. Among preferred fluorides there may be mentioned sodium fluoride but also the corresponding potassium or litium salts can be used.

In a conventional manner the composition may furthermore contain phosphates of different types in accordance with conventional techniques. Moreover, the composition according to the invention may contain other excipients, such as surface active substances, gelling agents and other constituents, such as flavouring, sweetening and colouring agents. Furthermore, the compositions according to the invention, which are presented in the form of tooth paste, may contain gelling agents, such as a natural or synthetic material. Among such materials there may be mentioned natural gums, such as locust bean gum, guar gum, xanthan gum and the like. Even if such non-ionic gums are preferred other materials may be used, for example tragant gum, sodiumcarboxymethyl cellulose, poly(vinylpyrrolidone), starch or the like. Such gelling agents are contained in the composition in a relatively small amount, for example from about 0.01 to 3 percent by weight of the composition.

Oral hygiene compositions according to the invention in the form of mouth washes can be presented as conventional gargles or can be presented in the form of containers designed as oral spray devices.

Additionally, the compositions according to the invention can contain as sweeteners for example saccarine, flavouring oils, such as peppermint oil, menthol, and colouring agents or white pigments, such as titanium dioxide, preserving agents, for example bensoates, antibacterial substances, such as chlorohexidin.

According to another aspect of the invention there is provided also a process for improving oral hygiene in mammals including man, and in this process there is administered orally to a mammal in need of treatment a biologically active amount of an oral hygiene composition as defined above.

The process according to the invention is suitable for the treatment of periodontitis, plaques and/or caries.

According to yet another aspect of the present invention it resides in the use of chitosan in combination with a sulphated, negatively charged polysaccharide for the manufacture of a dentally active oral hygiene composition as has been defined above. It is particularly preferred in this use that the chitosan is present in combination with heparin.

The expression "minor amount" used in the present disclosure in connection with proportions between constituents present refers to an amount less than about 50 percent by weight based on the composition as a whole.

The present invention will in the following be further illustrated by non-limiting examples, wherein percentages or proportions refer to weight unless otherwise indicated.

MATERIALS USED

Chitosan

Chitosan is a linear 1.4-bound polysaccharide built from free and N-acetylated β-D-glucosamine units. It is manufactured by N-deacetylation of chitin, a polymer forming the shell of inter alia insects and crab fish. The degree of deacetylation can be controlled by hydrolysis using alkali. In the present case the chitosan is used in the form of commercially available hydrochloric salts of about 20%, 50% and 85% N-deacetylation.

Sulphated polysaccharides

The preferred polysaccharide is the proteoglycane heparin (Pig mucosa, Kabi Vitrum) and other polysaccharides used are of a commercial type available on the market.

EXAMPLE 1

Film of chitosan-heparin 5 g HCl salt of chitosan of 50% deacetylation (Pronova Biopolymers, Seacure Cl 411) or of 85% deacetylation (Pronova Biopolymers, Seacure Cl 313) are dissolved in distilled water (0.5 L, 1% w/v). The film is prepared in petri-dishes having a surface of 54 $cm^2$. 20 mL of the solution is poured into the bowl and the film is then allowed to dry in a drying cabinet at 70° C. for 16 h. The film is then neutralized using a sodium phosphate buffer, 0.2M, pH 9, added to the petri-dish at room temperature. The film is allowed to stay in the buffer for 3–4 h and is then washed 3–4 times using 50 mL distilled water and is allowed to dry at room temperature.

A heparin solution is prepared according to the following:

To 100 mL 0.15M sodium chloride there is added 25 mg nitrite degraded heparin (Pig mucosa, Kabi Vitrum). The pH is adjusted to 3.9 using 0.1M hydrochloric acid, and 5 mg sodium cyanoborohydride are added to the solution. The chitosan film is left in this solution under shaking over night. The film is then washed with 50 mL distilled water 3–4 times.

EXAMPLE 2

Gel pearls of chitosan-heparin

A solution (2% w/v) of chitosan of 85% deacetylation (Pronova Biopolymers, Seacure Cl 313) is drop-wise pumped through a capillary (0.8 mm inner diameter) down into a sodium phosphate buffer, 0.1M, pH 7, 250 mL. Gel pearls of chitosan having a diameter of about 1.2 mm are formed.

After filtering on a glass filter and drying, the diameter of the balls is reduced to about 0.8 mm. Heparin is attached to the balls by ionbinding by admixing heparin, 1 g/L, in the buffer used.

EXAMPLE 3

Gel of chitosan-methyl cellulose-heparin 100 mg heparin are added to 100 mL distilled water with mixing. To the solution obtained there are added 50 mL of an aqueous solution of methyl cellulose (2% w/v) under stirring. To the solution obtained there is then added 50 mL chitosan (2% w/v, 50% deacetylation) also under stirring. Stirring is maintained for another 10 minutes, a coherent gel being obtained.

EXAMPLE 4

Film of chitosan-heparin, covalently bound

A neutralized chitosan film made in accordance with the description of Example 1 is immersed in 20 mL of a solution wherein it is allowed to remain for 24 h. The solution consists of 4.4 g sodium chloride and 125 mg periodate oxidized heparin in 0.5 L of water. The pH is adjusted to 3.9 with 0.5M hydrochloric acid, and then 15 mg of sodium cyanoborohydride is added. The film treated in this manner is then washed with water 3–4 times and is allowed to dry.

EXAMPLE 5

Film of chitosan-heparin, ion bound

To a neutralized chitosan film made in accordance with Example 1 there is added 20 mL of a solution consisting of 125 mg heparin dissolved in 0.5 L of water containing 4.4 g sodium chloride, the pH being adjusted to 3.9 with the use of 0.5M hydrochloric acid. Film and solution are allowed to stand in room temperature for 14 h. The film obtained is then washed with water 3–4 times and allowed to dry.

EXAMPLE 6

Tooth paste

A tooth paste is prepared as follows:

| Ingredients | Percentage |
| --- | --- |
| Sugar solution (50% solution of sorbitol, saccarin) | 25 |
| Glycerol | 8 |
| Titanium dioxide | 1.5 |
| Thickening agent, silica | 5 |
| Grinding agent, alumina | 12 |
| Surfactant | |
| Flavour | 0.5 |
| Gel according to Example 3 | 10 |
| Water | 37 |
| | 100 |

The ingredients above are mixed in a suitable apparatus in a conventional manner whereafter, if necessary, the pH is adjusted to about neutral.

EXAMPLE 7

Tooth powder

Heparin (Pig mucosa) in pulverulent form is admixed with chitosan (50% deacetylation, Pronova Biopolymers, Seacure Cl 411) to form a fine-grained dry powder useful as an oral hygiene composition.

EXAMPLE 8

Mouth wash

| Ingredients | Percentage |
| --- | --- |
| Ethanol | 8 |
| Glycerol | 4 |
| Flavours | 0.1 |
| Gel according to Example 3 | 5 |
| Water | 82.9 |
| | 100.0 |

The ingredients are mixed in the proportions given to form a slightly cloudy mouth wash.

EXAMPLE 9

Clinical test of tooth powder

The tooth powder according to Example 7 is used in connection with tooth brushing daily for 2 months for the purpose of studying the influence on the general tooth status and the condition of the periodontal pockets of the subject under test. The result after two months tooth brushing was the following according to the evaluation made by tooth technicians:

| Periodontal pockets | Pocket depth |
| --- | --- |
| 10 pockets | 1 mm deeper |
| 31 pockets | unchanged |
| 45 pockets | 1 mm reduction |
| 6 pockets | 2 mm reduction |
| 4 pockets | 3 mm reduction |
| 3 pockets | 4 mm reduction |

Furthermore, no visible inflammation could be observed and, in addition, X-rays taken of the front teeth of the subject indicate newly formed tissue around the teeth. Since the development of periodontal pockets to an increased depth normally in accordance with conventional art can be retarded but rarely reversed the results presented above are unexpected and essential.

EXAMPLE 10

Clinical test using tooth paste

The test according to Example 9 is repeated, this time using the tooth paste manufactured according to Example 6. The results obtained are similar to those obtained in Example 9. Furthermore, there is obtained as a result of the modified brushing of the teeth a clear plaque-reducing effect in relation to normal teeth brushing using normal tooth paste. This reduction of plaque results in a clear regression of the gingival inflammation, and a distinct mobility reduction could also be observed.

EXAMPLE 11

Clinical test using film

In relation to a factual periodontal pocket a surgical incision was performed residing in cutting, after anaesthesia, with a scalpel in the gingiva along the outside of the tooth and the inside the tooth in the area involved. The gingiva is folded out from the tooth and the root surface of the tooth having plaque deposited thereon is exposed. The root surface is now cleaned with an instrument for removal of plaque, and after cleaning and washing using sterile solutions the chitosan-heparin film made in accordance with Example 1 is applied locally, and the gingiva is then stitched back onto the surface of the tooth.

In connection with healing reduced inflammation, reduced pathological pocket depth, reduced mobility and improved attachment by X-ray could be observed.

EXAMPLE 12

Clinical test using gel pearls

The procedure in Example 11 is repeated, in this instance while using gel pearls of chitosan-heparin manufactured according to Example 2. Similar results are obtained.

EXAMPLE 13

Clinical test using gel

The procedure of Example 11 is repeated, this time while using the gel of chitosan-methylcellulose-heparin prepared according to Example 3. Similar results to those of Example 11 can be observed.

EXAMPLE 14

Mouth-wash

Example 8 is repeated while using dermatan sulphate as a sulphated polysaccharide instead of heparin.

EXAMPLE 15

Clinical test using tooth powder

Example 9 is repeated in this case using a tooth powder according to Example 7 wherein heparin is replaced with condroitin-6-sulphate.

EXAMPLES 16–20

Test for antibacterial activity using solutions

The following solutions are prepared:

1) Dextransulphate (Pharmacia, 1 g) is dissolved in 200 mL of distilled water. To the stirred solution are added 50 mL of an aqueous solution of methylcellulose (2% w/v) and 250 mL of chitosan (2% w/v, with a degree of deacetylation of 59%).
2) To water (200 mL) are added 50 mL of an aqueous solution of methylcellulose (2% w/v) and 250 mL of chitosan (2% w/v, with a degree of deacetylation of 59%).
3) Heparin (1 g) is dissolved in 200 mL of distilled water. To the stirred solution are added 50 mL of an aqueous solution of methylcellulose (2% w/v) and 250 mL of chitosan (2% w/v, with a degree of deacetylation of 59%).
4) Heparin (Pig mucosa, Kabivitrum, 1 g) is dissolved in 450 mL of distilled water. To the stirred solution is added 50 mL of an aqueous solution of methylcellulose (2% w/v).
5) Dextransulphate (Pharmacia, 1 g) is dissolved in 450 mL of distilled water. To the stirred solution is added 50 mL of an aqueous solution of methylcellulose (2% w/v).

The solutions are tested for antibacterial activity in blood bowls coated with saliva diluted 1:10 and dried in an incubator for 30 min before use. Longitudinal grinding sections of teeth exposing enamel and cement are immersed in the respective test solutions for 5 min at 37° C. and then transferred to sterile physiological salt water for up to 3 h. At 0 min, 15 min, 30 min, 1 h, 2 h, 3 h one grinding section from each test series is removed and placed on two coated blood bowls. A negative control is placed in the centre of each bowl.

The antibacterial activity of the respective solutions is evaluated according to a score from 0 to 3. Solutions 1, 2 and 3 of Examples 16, 17 and 18, respectively, are selectively antibacterial after 30 min rinsing and keep their antibacterial activity during the test period of 3 h. The results are summarized in the following table.

TABLE

| Example | Solution | Score |
|---|---|---|
| 16 | 1 | 3 |
| 17 | 2 | 2 |
| 18 | 3 | 3 |
| 19 | 4 | 0 |
| 20 | 5 | 0 |

It can be seen from the table above that using solutions containing only heparin or dextran sulphate in addition to mehtylcellulose express no observable anti-bacterial activity, whereas solutions combining either chitosan and dextran sulphate or chitosan and heparin show the highest score. Since, in addition to methylcellulose, solely chitosan shows a lower score the test results indicate a synergistic effect by the combination of chitosan and the sulphated negatively charged polysaccharides.

As is clear from performed clinical tests the use of the techniques according to the present invention induces essential and unexpected improvements in relation to the course of healing in connection with oral problems residing in periodontitis, formation of plaque and other inflammatoric conditions. Even though the present invention is not regarded to be restricted to any particular scientific theory or mechanism of action it is conceivable that the main constituents chitosan and sulphated, negatively charged polysaccharide present in the oral hygiene composition have such effect on the bacterial flora in the oral cavity or result in such enrichment of growth factors that the different healing processes are substantially promoted and accelerated. The invention is not restricted to the preferred embodiments as exemplified and the scope of the invention is limited only by the appended claims.

What is claimed is:

1. A method for the treatment of periodontitis, plaque or dental caries, said method comprising topically exposing the teeth or gums of a mammal in need of such treatment to an oral hygiene composition comprising chitosan in combination with a sulphated, negatively charged polysaccharide and dentally acceptable carrier, wherein the amount of said composition is effective to treat periodontitis, plaque or dental caries.

2. The method according to claim 1, wherein the weight ratio chitosan-polysaccharide lies within the range about 6:4 to 99.5:0.5.

3. The method according to claim 1, wherein the polysaccharide is selected from the group consisting of heparin, sucralfat, condroitin sulphates, dermatan sulphate, keratan sulphate and pentosan sulphates.

4. The method according to claim 3, wherein the polysaccharide is heparin.

5. The method according to claim 1, wherein the combination is in the form of a tooth cream, tooth paste or a tooth powder.

6. The method according to claim 1, wherein the combination is in the form of a mouth wash.

7. The method according to claim 1, wherein the combination is in the form of a mouth spray.

8. The method according to claim 1, wherein the combination is in the form of a degradable film, in the form of a gel, in the form of pearls or in the form of a powder.

9. The method according to claim 1, wherein the chitosan is present in combination with a polysaccharide selected from the group consisting of heparin, sucralfat, condroitin sulphates, dermatan sulphate, keratan sulphate and pentosan sulphates.

10. The method according to claim 9, wherein the chitosan is present in combination with heparin.

11. The method according to claim 2, wherein the polysaccharide is selected from the group consisting of heparin, sucralfat, condroitin sulphates, dermatan sulphate, keratan sulphate and pentosan sulphates.

12. The method according to claim 2, wherein the combination is in the form of a degradable film, in the form of a gel, in the form of pearls or in the form of a powder.

13. The method according to claim 3, wherein the combination is in the form of a degradable film, in the form of a gel, in the form of pearls or in the form of a powder.

14. The method according to claim 4, wherein the combination is in the form of a degradable film, in the form of a gel, in the form of pearls or in the form of a powder.

15. The method according to claim 11, wherein the combination is in the form of a degradable film, in the form of a gel, in the form of pearls or in the form of a powder.

16. An oral hygiene composition for the treatment of periodontitis, plaque or dental caries, said composition comprising an effective amount to treat periodontitis, plaque or dental caries of chitosan in combination with a sulphated, negatively charged polysaccharide and a dentally acceptable carrier.

* * * * *